(12) United States Patent
Caldwell

(10) Patent No.: US 12,220,333 B2
(45) Date of Patent: *Feb. 11, 2025

(54) MEDICAL DEVICE WITH ADJUSTABLE LENGTH

(71) Applicant: BOSTON SCIENTIFIC SCIMED, INC., Maple Grove, MN (US)

(72) Inventor: Caleb Caldwell, Fort Wayne, IN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 127 days.

This patent is subject to a terminal disclaimer.

(21) Appl. No.: 17/951,673

(22) Filed: Sep. 23, 2022

(65) Prior Publication Data

US 2023/0012922 A1 Jan. 19, 2023

Related U.S. Application Data

(63) Continuation of application No. 15/411,584, filed on Jan. 20, 2017, now Pat. No. 11,484,421.

(60) Provisional application No. 62/280,980, filed on Jan. 20, 2016.

(51) Int. Cl.
*A61F 2/82* (2013.01)
*A61F 2/04* (2013.01)
*A61F 2/95* (2013.01)

(52) U.S. Cl.
CPC .............. *A61F 2/82* (2013.01); *A61F 2/04* (2013.01); *A61F 2/95* (2013.01); *A61F 2002/048* (2013.01); *A61F 2250/0007* (2013.01); *A61F 2250/006* (2013.01); *A61F 2250/0097* (2013.01)

(58) Field of Classification Search
CPC ................................................ A61F 2002/048
See application file for complete search history.

(56) References Cited

U.S. PATENT DOCUMENTS

| 4,643,716 | A | 2/1987 | Drach |
| 4,790,810 | A | 12/1988 | Pugh et al. |
| 5,681,274 | A | 10/1997 | Perkins et al. |
| 5,795,319 | A | 8/1998 | Mohammed |
| 6,656,146 | B1 | 12/2003 | Clayman et al. |
| 7,291,180 | B2 * | 11/2007 | St. Pierre .......... A61M 25/0009 623/23.65 |
| 7,951,206 | B2 | 5/2011 | St. Pierre |

(Continued)

FOREIGN PATENT DOCUMENTS

| WO | 2012027508 A2 | 3/2012 |
| WO | 2016131938 A1 | 8/2016 |

OTHER PUBLICATIONS

"Stretch™ VL Flexima". Boston Scientific, http://bostonscientific.com/en-US/products/stents-ureteral/stretch-vl.html (Apr. 2014).

(Continued)

*Primary Examiner* — Jacqueline Woznicki
(74) *Attorney, Agent, or Firm* — Seager, Tufte & Wickhem, LLP (57) ABSTRACT

An adjustable length medical device, such as a drainage stent, and delivery device for placing within the body, having an elongate tube and retention members at each end portion for anchoring the device in the body. The proximal portion of the device including the proximal retention member may be segmented in incremental portions so that the length of the device can be adjusted for placement.

15 Claims, 3 Drawing Sheets

(56) References Cited

U.S. PATENT DOCUMENTS

| | | | |
|---|---|---|---|
| 8,007,702 B2* | 8/2011 | Gellman | A61F 2/04 |
| | | | 623/23.69 |
| 8,597,367 B2 | 12/2013 | Dillinger | |
| 8,728,169 B2 | 5/2014 | Li | |
| 2004/0059279 A1 | 3/2004 | McWeeney et al. | |
| 2008/0234659 A1* | 9/2008 | Cheng | A61L 29/148 |
| | | | 604/523 |
| 2009/0281635 A1* | 11/2009 | Li | A61M 27/008 |
| | | | 427/2.25 |
| 2012/0095566 A1* | 4/2012 | Teague | A61F 2/04 |
| | | | 623/23.7 |

OTHER PUBLICATIONS

International Search Report and Written Opinion issued on (Mar. 21, 2017), for PCT/US2016/012017 (10 pages).
https://web.archive.org/web/20140521223 11/http://www.bostonscientific.com/en-US/products/stents—ureteral/stretch-vl.html (accessed Aug. 20, 2017).

* cited by examiner

MEDICAL DEVICE WITH ADJUSTABLE LENGTH

CROSS-REFERENCE TO RELATED APPLICATIONS

This application is a continuation of and claims the benefit of the earlier filing date of U.S. patent application Ser. No. 15/411,584, filed on Jan. 20, 2017, which claims the benefit of priority under 35 U.S.C. § 119 to U.S. Provisional Application Ser. No. 62/280,980, filed Jan. 20, 2016, and which applications are incorporated herein by reference in their entireties for all purposes.

TECHNICAL FIELD

The present disclosure relates generally to medical devices with adjustable or variable length, particularly to medical stents, and more particularly to devices placed in the body to stent the ureter and facilitate drainage from the kidney to the bladder.

BACKGROUND

Medical devices developed for implantation or insertion into patients are known for various purposes including stenting, drainage, etc. of lumens, tracts, vessels, and cavities within the body. As an example, polymeric ureteral stents are widely used to facilitate drainage in the upper urinary tract (e.g., drainage from the kidney to the bladder), for example, following ureteroscopy, endourerotomies, and endopyelotomy for ureteral strictures, as well as in other instances where ureteral obstruction may occur.

Figure 1:
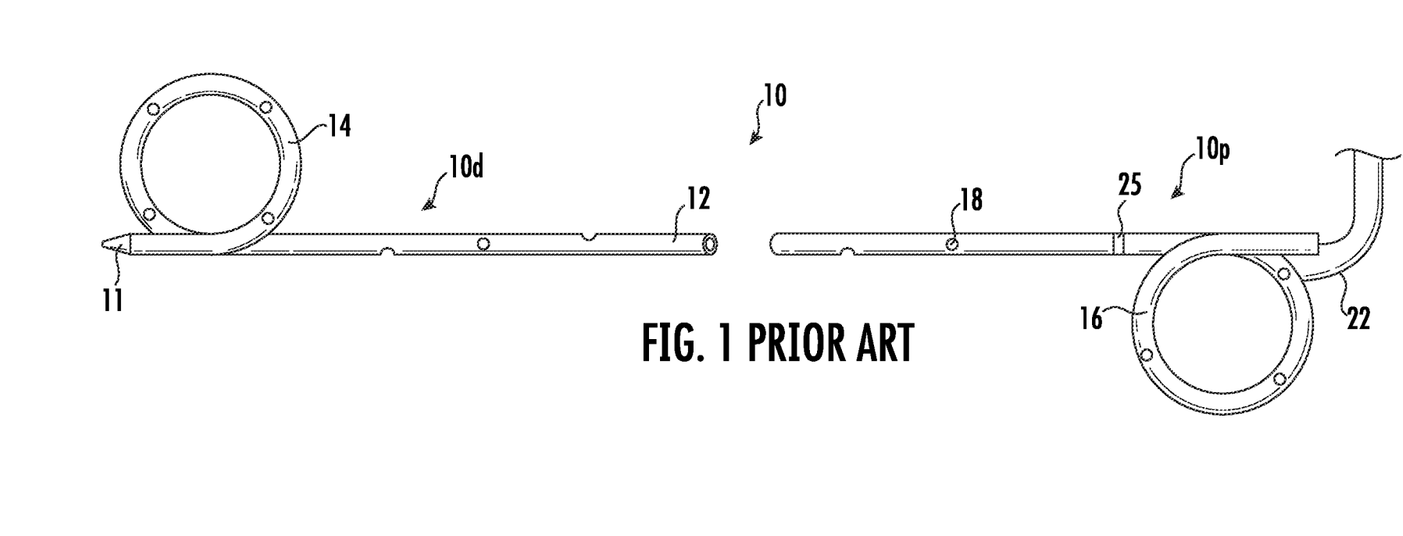
FIG. 1 is an illustration of a ureteral stent, according to the prior art.

An exemplary stent 10 of this type is illustrated in FIG. 1. The stent 10 has a proximal end 10p and a distal end 10d. It is a tubular polymer extrusion having a shaft 12, a distal renal retention structure (e.g., renal "pigtail" 14), and a proximal retention structure (e.g., bladder "pigtail" 16). These retention structures prevent upward migration of the stent toward the kidney or downward migration of the stent toward the bladder. Once properly deployed in the ureter, the stent 10 provides ureteral rigidity and allows the passage of urine. The stent 10, as exemplified by FIG. 1, may further be provided with any one or more of the following: (a) a tapered tip 11, to aid insertion, (b) multiple side ports 18 (one numbered), which are typically arranged in a spiral pattern down the length of the body to promote drainage, (c) graduation marks 25 (one illustrated), which are normally used for visualization by the physician to know when the appropriate length of stent has been inserted into the ureter, and (d) a suture 22, which aids in positioning and withdrawal of the stent.

Figure 2:
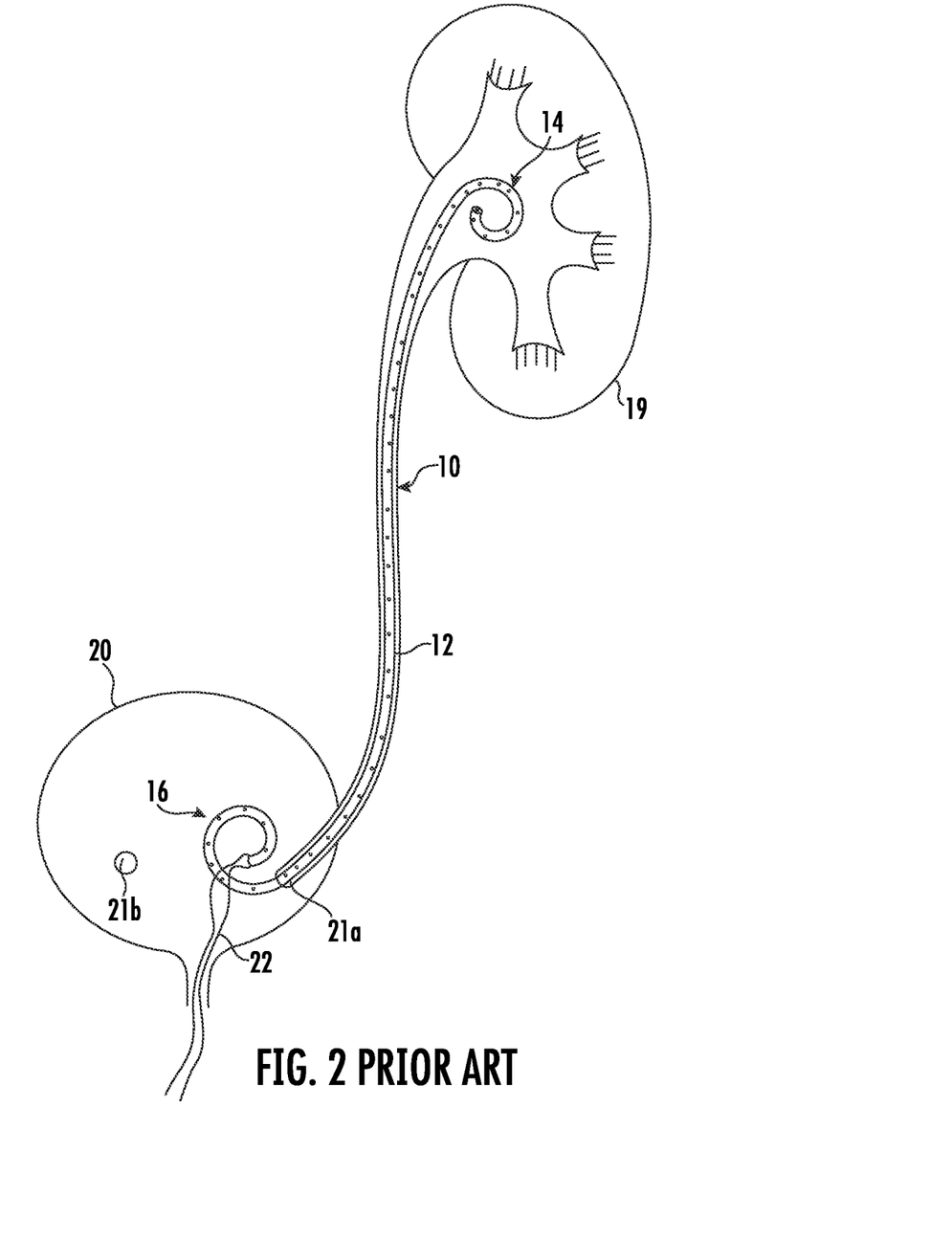
FIG. 2 is an illustration of a ureteral stent, like that of FIG. 1, positioned in the body

During placement, such ureteral stents 10 are typically placed over a urology guide wire, through a cystoscope or flexible ureteroscope, and advanced into position with a pusher. Once the distal end of the stent is advanced into the kidney/renal calyx, the guide wire is removed, allowing the pigtails 14, 16 to form in the kidney 19 and bladder 20, as shown in FIG. 2. The renal pigtail 14 of the stent may be closed or tapered on the end, depending on the method of insertion (e.g., the use of a guide wire or otherwise). As shown in FIG. 2, the stent 10 extends through the ureteral orifice 21a and into the bladder 20. For clarity, the ureter entering bladder 20 through the opposite ureteral orifice 21b is not shown.

These types of implanted medical devices may be associated with patient discomfort or pain after being positioned within the body, for example, in regard to ureteral stents, pain and/or discomfort in the bladder and flank area after insertion. Another issue is that various applications and anatomies require medical devices of different diameters and lengths, e.g., differences in individual ureteral anatomies require different diameters and lengths between the end retention structures of ureteral stents. Consequently, hospitals and other facilities inventory stents of different diameters and for each diameter, stents of different lengths, in some cases as much as six stents of different lengths for each diameter.

Generally, a physician must estimate ureter length before beginning a procedure. If the estimate is near the end of a particular length range, it is possible to select a stent that is slightly too long or too short. However, that fact may not be ascertainable until the stent has been implanted. The procedure for correcting any incorrect selection involves removing that stent and placing a longer or shorter stent in the ureter thereby complicating the procedure and potentially increasing patient trauma.

Examples of variable length stents include offset or planar coils at one or both of the end retention structures that can be unwound to increase or decrease the effective length between the structures. Another ureteral stent example includes a serpentine planar extension at the bladder end of the stent, and individual sections of the serpentine extension can be straightened to extend the effective length of the stent. Further examples disclose multi-turn coils at the bladder end that may be clipped off outside of the body when the length of the stent has been estimated by the physician.

Although these examples may reduce inventory requirements, excess retention structure left in the bladder may occupy a considerable volume which may increases a risk of tissue irritation. Additionally, stents clipped to length outside of the body prior to placement without reference markings may ultimately result in a length that is too short, requiring a new stent to be used, or too long, in which case the excess material and irritation concerns remain. Therefore, there exists a need for an adjustable length medical device, which may be sized accurately and consistently without excess volume leftover that may cause irritation.

SUMMARY

One aspect of the present disclosure is an improved adjustable or variable length medical stent, e.g., ureteral stent, in which a retention structure occupies a minimal volume, minimizes the potential for tissue irritation once implanted, and facilitates implantation and removal. Another aspect of the present disclosure is an adjustable length medical device, such as a ureteral stent, that minimizes inventory requirements.

A further aspect of the present disclosure is a medical device comprising an elongated flexible tubular member having a lumen extending along a length thereof, the tubular member forming proximal and distal retention members at respective proximal and distal end portions of the tubular member, and an intermediate portion of the tubular member extending between the end portions; the proximal retention member and proximal portion configured to be segmented in incremental portions.

The above and below embodiments and other embodiments of the present disclosure may include one or more of the following: the proximal retention member and proximal portion may be configured to be segmented in incremental portions in vivo; the proximal retention member and proximal portion may include graduated markings along the length thereof that correspond to the incremental portions; the wall of the tubular member may have relief portions corresponding to the incremental portions to facilitate segmenting; the relief portions may include one or more of a reduced diameter of the wall, perforations of the wall, or scoring of the wall; the proximal retention member may include multiple turns wound upon each other within a single plane that is parallel to a longitudinal axis of the intermediate portion; each of the multiple turns of the proximal retention member may be wound about a turn axis that is transverse to the longitudinal axis of the intermediate portion; the distal retention member may comprise a single pigtail wound in a plane that is offset from the plane that is parallel to the longitudinal axis of the intermediate portion; drainage elements may be arranged along an exterior of the tubular member and communicate with the lumen; the device may be a ureteral stent.

Another aspect of the present disclosure is a ureteral stent comprising an elongated flexible tubular member having a lumen extending along a length thereof, the tubular member forming bladder and renal retention members at respective proximal and distal end portions of the tubular member, and an intermediate portion of the tubular member extending between the end portions; the bladder retention member and proximal portion configured to be segmented in incremental portions.

The above and below embodiments and other embodiments of the present disclosure may include one or more of the following: the bladder retention member and proximal portion may include graduated markings along the length thereof that correspond to the incremental portions; a wall of the tubular member may have relief portions corresponding to the incremental portions to facilitate segmenting; the relief portions may include one or more of a reduced diameter of the wall, perforations of the wall, or scoring of the wall; the graduated markings may be spaced apart at even intervals starting from a distalmost marking that is a known distance from the distal end of the stent; the known distance may be 10 cm, and the even interval may be 2 cm.

Yet another aspect of the present disclosure is a stent kit comprising a ureteral stent and a delivery device: the stent including an elongated flexible tubular member having a lumen extending along a length thereof, the tubular member forming bladder and renal retention members at respective proximal and distal end portions of the tubular member, an intermediate portion of the tubular member extending between the end portions, and the bladder retention member and proximal portion configured to be segmented at incremental portions along the length thereof; the delivery device including an inner elongate delivery member, the stent slidably disposed coaxially about an exterior surface of the inner member for placement of the stent in a ureter, an outer elongate pusher member slidably disposed coaxially about the inner member proximal to the stent, the pusher configured to abut the proximal end of the stent and push it distally along the inner member during placement, and a segmenting member configured to segment the bladder retention member or proximal portion at a selected one of the incremental portions.

The above and below embodiments and other embodiments of the present disclosure may include one or more of the following: the bladder retention member and proximal portion may include graduated markings along the length thereof that correspond to the incremental portions; a wall of the tubular member may relief portions corresponding to the incremental portions to facilitate segmenting.

Another aspect of the present disclosure is a method of placing a drainage stent in a body comprising inserting the stent into the body until it is positioned at a desired point of placement, the stent including an elongated flexible tubular member having a lumen extending along a length thereof, the tubular member forming proximal and distal retention members at respective proximal and distal end portions of the tubular member, the proximal retention member and proximal portion including graduated markings corresponding to incremental portions along the length thereof; identifying a graduated marking that approximates a desired length of the stent based on the length of the placement point; and adjusting the stent to the desired length by segmenting the stent at the incremental portion that corresponds to the identified graduated marking.

BRIEF DESCRIPTION OF THE DRAWINGS

In the drawings, like reference characters generally refer to the same parts throughout the different views. Also, the drawings are not necessarily to scale, emphasis instead being placed upon illustrating principles of the present disclosure. The present disclosure, and exemplary embodiments according to the disclosure, are more particularly described in the following description, taken in conjunction with and in reference to the following drawings, in which.

DETAILED DESCRIPTION

Devices, systems and methods in accordance with various embodiments of the present disclosure include medical devices which are adjustable to a desired length. The devices include an elongated flexible tubular member having a lumen extending along a length thereof, the tubular member forming proximal and distal retention members at respective proximal and distal end portions of the tubular member, and an intermediate portion of the tubular member extending between the end portions. The proximal retention member and proximal portion are configured to be segmented in incremental portions from the remainder of the device in order to adjust the device to a desired length.

Figure 3:
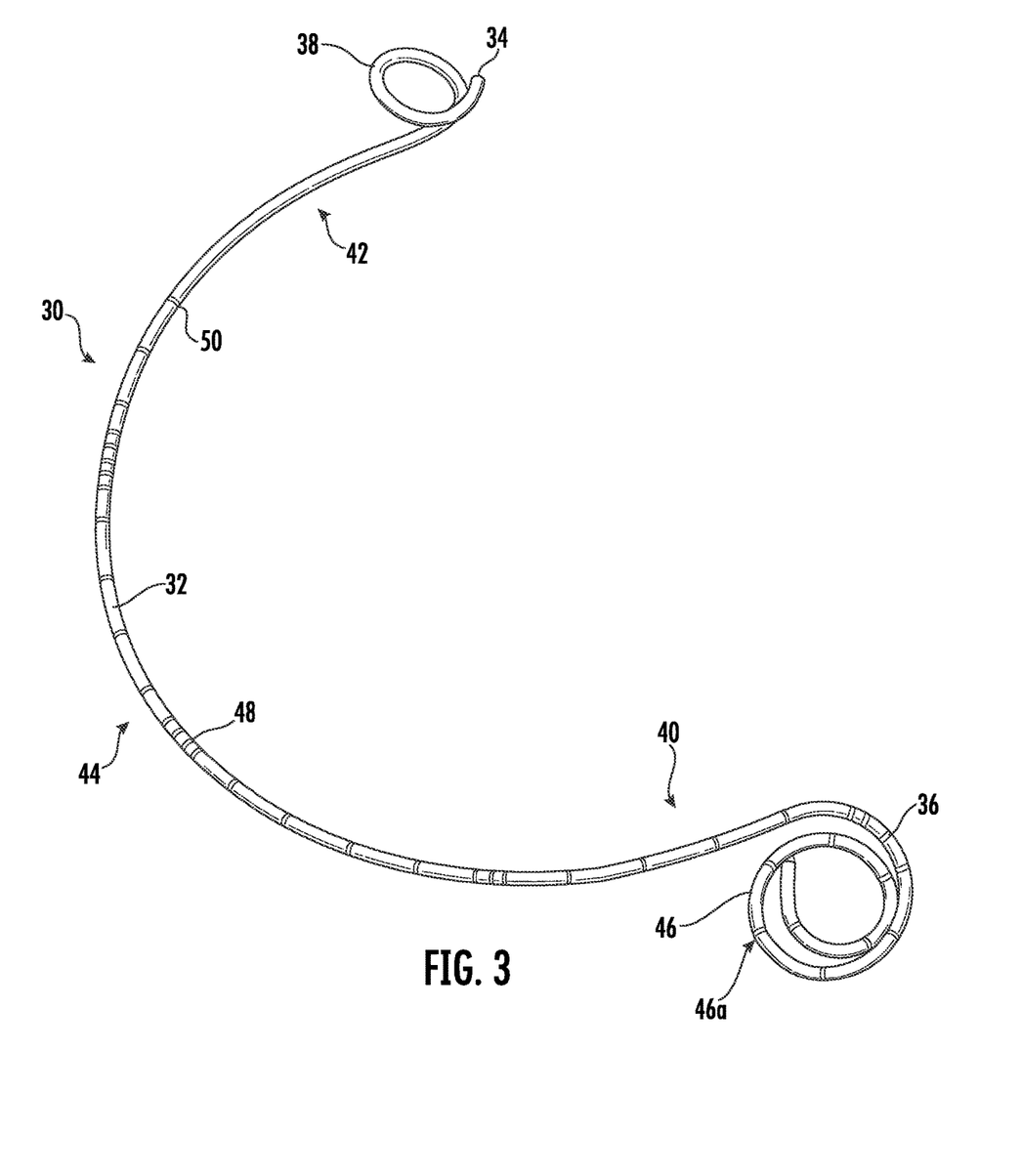
FIG. 3 illustrates an adjustable length medical device in accordance with embodiments of the present disclosure.

Various embodiments according to the present disclosure are described below and with reference to the exemplary configuration of a ureteral stent as depicted in FIG. 3. As used herein, "proximal end" refers to the end of the object that lies closest to the medical professional or outside the urethral exit (downstream) in the case of a ureteral stent, and "distal end" refers to the end of an implanted or inserted object that lies furthest from the medical professional or urethral exit (upstream) when used in the context of a ureteral stent.

With reference to FIG. 3, an adjustable length ureteral stent 30 is depicted. The stent 30 includes an elongated flexible tubular member 32 having a lumen 34 extending along a length thereof. The tubular member forms a bladder (proximal) retention member 36 and renal (distal) retention member 38 at the respective proximal end portion 40 and distal end portion 42 of the tubular member 32. An intermediate portion 44 of the tubular member extends between the end portions. The bladder retention member 36 and proximal portion 40 are configured to be segmented in incremental portions (e.g., 46) from the remainder of the stent to adjust the device to a desired length.

With continued reference to FIG. 3, the tubular member may include graduated markings (e.g., 48) along the length thereof starting from a distalmost marking (50) that is spaced a known distance from the distal end of the stent. The graduated markings along the length of the bladder retention member and proximal portion may correspond to incremental portions (e.g., 46). The wall of the tubular member may include relief portions (e.g., 46a) corresponding to the incremental portions (e.g., 46) to facilitate segmenting. The proximal retention member and proximal portion may be segmented in incremental portions in vivo or ex vivo.

In this and other embodiments, the relief portions (e.g., 46a) may include one of more of a reduced diameter of the wall, perforations of the wall, or scoring of the wall. The proximal retention member may comprise multiple turns (such as the bladder retention member 36 of FIG. 3) wound upon each other within a single plane that is parallel to a longitudinal axis of the intermediate portion 44. In such embodiments, each of the multiple turns of the proximal retention member may be wound about a turn axis that is transverse to the longitudinal axis of the intermediate portion.

The distal retention member (such as the renal retention member 38 of FIG. 3) may comprise a single pigtail wound in a plane that is offset from the plane that is parallel to the longitudinal axis of the intermediate portion 44. Other examples of retention structures for use with this or other embodiments of the present disclosure include, for example, spirals, coils, corkscrews, malecots, barbs, mushrooms and hook ends, among others.

Drainage elements (not shown in FIG. 3) may be arranged along an exterior of tubular member 32 and in fluid communication with lumen 34 of tubular member to facilitate drainage of fluid along the interior and exterior of the device. The elements may be holes or other shapes. Additionally or alternatively to the drainage elements, channels may be included on the exterior to increase the drainage capabilities of the device. Channels may assume various shapes and configurations, such as semicircular, triangular, rectangular and trapezoidal cross-sections, respectively, among many other shapes.

The various embodiments of adjustable length medical devices according to the present disclosure, including as described above and below, may have any of the following features. Devices, particularly in the context of a ureteral stent, may have an outer diameter of about 3 French to about 9 French, including any half or whole size within that range, and may have an inner diameter of about 0.38 inches to accommodate the profile of standard medical guidewires within the lumen of the tubular member. Embodiments of the present disclosure for use as ureteral stents may have an adjustable length of about 20 cm to about 35 cm as measured between the retention members.

Devices may include a coating on the exterior and/or interior of the tubular member, which may in certain examples be a hydrophilic or hydrophobic coating, depending on the desired handling characteristics to be imparted to the device. Such a coating may be applied after extrusion or be integral to the manufacture of the tubing used to construct the device.

One or both of the ends of the lumen 34 at the proximal and distal end portions (40, 42) of a device may be closed or open, tapered or non-tapered. The lumen 34 may have a cross section along the length of the tubular member that is circular, non-circular, symmetric or asymmetric.

Materials of the tubular member may be polymeric in various embodiments of the present disclosure. Polymeric materials suitable for embodiments of the tubular member may comprise any polymer or polymer blend suitable for use in implantable or insertable medical devices. Polymers may be selected, for example, from suitable members of the following, among others: polyolefins such as polyethylenes (e.g., metallocene catalyzed polyethylenes), polypropylenes and polybutylenes; polyolefin copolymers, e.g., ethylenic copolymers such as ethylene vinyl acetate (EVA) copolymers, ethylene-methacrylic acid copolymers and ethylene-acrylic acid copolymers, where some of the acid groups can be neutralized with either zinc or sodium ions (commonly known as ionomers); vinyl aromatic polymers such as polystyrene; vinyl aromatic copolymers such as copolymers of olefins and styrene or alpha-methyl styrene, for example, butadiene-styrene copolymers and copolymers of polyisobutylene with polystyrene or polymethylstyrene, for example, polystyrene-polyisobutylene-polystyrene triblock copolymers; polyacetals; chloropolymers such as polyvinyl chloride (PVC); fluoropolymers such as polytetrafluoroethylene (PTFE); polyesters such as polyethyleneterephthalate (PET); polyester-ethers; polyamides such as nylon 6 and nylon 6,6; polyethers; polyamide ethers such as polyether block amides (PEBA) comprising (a) nylon blocks, for example, nylon 6, nylon 4/6, nylon 6/6, nylon 6/10, nylon 6/12, nylon 11 or nylon 12 blocks and (b) polyether blocks, for example, poly(ethylene oxide), poly(trimethylene oxide), poly(propylene oxide) or poly(tetramethylene oxide) blocks, one specific example of which is a poly(tetramethylene oxide)-b-polyamide-12 block copolymer, available from Elf Atochem as PEBAX; polyoctenamers such as Vestenamer® from Degussa Corp., Parsippany, N.J., which is a mixture of cyclic and linear polyoctenamers; elastomeric and thermoplastic polyurethanes, including polyurethane copolymers (including block and random copolymers that are polyether based, polyester based, polycarbonate based, aliphatic based, aromatic based and mixtures thereof), commercially available examples of which include Carbothane®, Tecoflex®, Tecothane®, Tecophilic®, Tecoplast®, Pellethane®, Chronothane® and Chronoflex®); and vinyl aromatic polymers and copolymers; silicones; polycarbonates; as well as mixtures of any of the foregoing, among others.

EVA copolymers are one preferred group of polymers for use in ureteral stents. Examples include EVA copolymers having a vinyl acetate content of from about 5% to about 40% (including 5% to 10% to 15% to 20% to 25% to 30% to 35% to 40%, with 10-30% being typical). Increasing the vinyl acetate content typically results in a softer material, while decreasing the vinyl acetate content typically produces a harder material.

The medical device of various embodiments of the present disclosure may also contain one or more optional additives, for example, selected from therapeutic agents, radiopaque agents, colorants, other optional additives such as plasticizers and extrusion lubricants, and combinations of the above, among others, in amounts effective to serve their intended purposes. Where used in the devices of the present disclosure, such optional additives may be present, for example, in the polymeric materials such as those discussed above, among others, or in coatings applied to the polymeric materials, or both.

Radiopaque agents facilitate viewing of the medical device during insertion of the device and at any point while the device is implanted. Among radiopaque agents useful in the medical devices of the present disclosure are included bismuth salts such as bismuth subcarbonate, bismuth oxychloride, bismuth trioxide, barium sulfate, tungsten, and mixtures thereof. More specific examples of such radiopaque agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine, among others. Where present, the radiopaque agent is typically present in an amount of from about 10% to about 40% (including 10% to 15% to 20% to 25% to 30% to 35% to 40%, with 15-30% being more typical). Additionally or alternatively, the polymeric material or additive material choice, as well as extrusion technique, may be optimized to enhance device contrast using ultrasound imaging. The incorporation of sonographic agents, in addition to or as an alternative to radiopaque agents, such as contrast beads or foams, among other examples, facilitate viewing of the medical device under ultrasonic imaging during insertion of the device and at any point while the device is implanted. One skilled in the art can readily determine an appropriate radiopaque and sonographic agent content to achieve the desired visibility. The polymer materials described may be mixed with the radiopaque and/or the sonographic agents above, or a colorant. A colorant may be used as a visual cue to a medical professional about the location of the medical device in the patient.

Examples of optional therapeutic agents include antimicrobial agents, agents that reduce pain and discomfort, such as anti-inflammatory agents, analgesic agents, local anesthetic agents and antispasmodic agents, anti-cancer agents, and combinations thereof. The term "antimicrobial agent" as used herein means a substance that kills and/or inhibits the proliferation and/or growth of microbes, particularly bacteria, fungi and yeast. Antimicrobial agents, therefore, include biocidal agents and biostatic agents as well as agents that possess both biocidal and biostatic properties. Anti-inflammatory agents include steroidal and non-steroidal anti-inflammatory agents. Analgesic agents include narcotic and non-narcotic analgesics. Examples of anticancer drugs include alkyating agents, antimetabolites, antimitotics, hormones, immunosuppressives, natural products, and other agents. Specific examples of the categories of therapeutic agents enumerated here are described in U.S. Pat. Nos. 8,728,169 and 8,597,367, assigned to Boston Scientific Corporation, the entire disclosures of which are incorporated herein by reference.

In embodiments of the present disclosure where a therapeutic agent is provided within a polymeric material, the device may exhibit an extended release profile or rapid release profile. By "extended release profile" is meant a release profile by which an effective amount of therapeutic agent continues to be released at least one day after device implantation or insertion, for example, from 1 day to 2 days to 4 days to 1 week to 2 weeks to 1 month to 2 months to 6 months to 1 year or more after device implantation. By "rapid release profile" is meant a release profile by which the therapeutic agent is substantially all released (e.g., 75% to 90% to 95% or more is released) within 24 hours of implantation or insertion, for example, from 1 hour or less to 2 hours to 4 hours to 8 hours to 16 hours to 24 hours. In certain embodiments, prior to insertion or implantation, one (e.g., a physician or an assistant to the same) may spray the device with, or dip the device into, a therapeutic-agent-containing solution, thereby loading the device with the agent. The amount of therapeutic agent present, will depend, for example, upon the efficacy of the therapeutic agent employed, the release rate, and so forth. One skilled in the art can readily determine an appropriate therapeutic agent loading to achieve a desired outcome.

In various of the embodiments above and otherwise in accordance with the present disclosure, the tubular member of a medical device may include a single-piece, extruded body that is a single material having the same durometer value throughout the length of the device. Alternatively, an extruded body may include along the length a first section of a material having a first durometer value and a second section of a material having a second durometer value. The second durometer value may be greater than the first durometer value, such as a ureteral stent as described above with reference to FIG. 3, where the first section may correspond to the proximal portion and the bladder retention member and the second section may correspond to the distal portion and the renal retention member. A transition section of the extruded body (e.g., at a point along the intermediate portion 44 of the stent of FIG. 3) includes a co-extrusion of the first and second materials. For example, the "hard" material can be EVA having a durometer value of about 80 to about 95 on a Shore A scale, preferably about 87 to about 95 on a Shore A scale, and more preferably about 90 on a Shore A scale, and the "soft" material can be another type of EVA having a durometer value of about 70 to about 90 on a Shore A scale, preferably about 78 to about 90 on a Shore A scale, and more preferably about 86 on a Shore A scale. Interrupted layer extrusion techniques, gradient-type coextrusion techniques, or similar techniques can be used to produce the transition sections described above.

The retention members of devices according to various embodiments of the present disclosure may be formed by placing an extrusion of the elongate tubular body on a mandrel, shaped in a particular form. The extrusion may be formed into a desired shape by heating the extrusion while on the mandrel. Alternatively, the extrusion may be laid into a plate having a groove cut into it in the shape of the desired retention member. The plate may be heated from below (for example, with a heat lamp) to form the extrusion into a retention member shape according to the configuration of the groove. Both retention members may be formed at the same time using two adjacent plates, each with a groove for the retention member at either end of the medical device. The plates may be heated at different temperatures, to the extent necessary, for example, if the two ends of the device are made from different material(s), and may be heated for the same or different lengths of time.

Graduated markings (e.g., 48) and incremental portions (e.g., 46) may be spaced apart at even intervals starting from a distalmost marking (e.g., 50) that is a known distance from the distal end of a device, such as the ureteral stent depicted in FIG. 3. For example, the markings may start at a known distance of 10 cm from the distal end of the stent, and appear at even intervals of 2 cm from the 10 cm point along the length of the proximal retention member to the end of the proximal portion of the stent. Exemplary marking are depicted in FIG. 3. Intermediate single markings may be used to indicate interim 2 cm distances and incremental portions between other distance milestones that are delineated with multiple markings. For example, with reference to FIG. 3, five marks may indicate 10 cm from the distalmost marking, four marks may indicate 20 cm, three marks, 30 cm, and so forth. Other intervals, e.g., 1 cm, are contemplated. The intervals may be odd or even, or both. The distalmost point may start from some distance other than 10 cm. Markings may include printed or etched monolithic bands, multi-stripe bands, printed numeric indicators, or any combination of these elements. Applied markings may or may not be radiopaque and/or visible using ultrasound.

The medical professional when identifying the desired length of the device for segmenting may use the graduated markings to not only identify the incremental portion to segment, but also approximate the resulting length of the stent from the markings once the length is adjusted.

In various embodiments of the present disclosure, positioning of the medical device at a desired point of placement may be accomplished by different configurations of delivery devices known in the art. For example, with respect to a ureteral stent as an exemplary embodiment of the present disclosure, the distal end of the stent may be inserted through the bladder and ureter into the kidney. A medical professional may insert a guidewire through the bladder, ureter and up into the kidney. The stent is placed over the guidewire, thereby straightening the retention members on the wire. The stent slides along the guidewire, alone or is carried on a catheter or other delivery device that the wire extends through. The guidewire, if used alone, may be sufficiently stiff to hold the retention members straight while the guidewire is in the lumen of the stent. An outer pusher member slidably coaxial with an inner member of a delivery device, or with a wire if used alone, may be used to abut the proximal end of the stent and push the stent distally.

A radiopaque or sonographic band, filler or other marker as part of the pusher and/or delivery device allows a medical professional to view the pusher and/or device on a fluoroscope or using ultrasound. Additionally, if the stent is radiopaque or sonovisible, placement of the stent in the patient may be confirmed by viewing the stent on a fluoroscope or using ultrasound. Once positioned at distal end of the placement point, the guidewire alone or in conjunction with a delivery device, if used, is withdrawn from the lumen of the distal (or kidney, in the case of a ureteral stent) retention member. If a pusher is used, the pusher holds the stent in place while the guidewire or guidewire and inner member of the delivery device is removed. The shape-memory material from which the retention member is constructed allows the retention member to return to its shape memory configuration, such as a pigtail coil.

As the guidewire and/or delivery device is withdrawn into, for example, the bladder in the case of a ureteral stent, the medical professional sights the renal retention member and proximal portion including the graduated markings corresponding to incremental portions along the length thereof, identifying the graduated marking that approximates the desired length of the stent extending along the ureter at the placement point.

Once identified, the stent is adjusted to the desired length by segmenting the stent at the incremental portion that corresponds to the identified graduated marking. The segmenting may be done with a separate tool from the guidewire or delivery device or with a tool that is integrated therewith. Various segmenting tools are contemplated as suitable to segment a stent or other medical device at the desired incremental portion, such as cutting blades, cutting wires, heated wires or blades, grasping, punching, crimping or pinching mechanisms, or the like. Heated tools may include a mold to form a taper on the end of the tubular member after the incremental portions is segmented from the remainder of the device.

The segmenting may be accomplished while the stent is still in a straightened configuration on the guidewire or delivery device, or after the guidewire alone or in conjunction with a delivery device, if used, is withdrawn from the lumen of the proximal (or bladder, in the case of a ureteral stent) retention member and the retention member assumes its shape memory form, such as a multi-turn planar coil. The segmented incremental portion may be removed from the bladder through the urethra by various means.

A tapered tip on the distal retention member can facilitate inserting the device through the passages of a patient's body. Additionally, a medical professional can use a suture to reposition the stent (by pulling on it) when inserting the stent, and the medical professional can use a suture to remove the stent from the patient after some period of use, provided the suture is secured to a portion of the stent above any incremental portion that may be segmented. For example, a medical professional may leave the proximal end of the suture inside the patient's body or leave the end of the suture outside the body. When the stent is to be removed, the medical professional may pull on the suture to remove the stent. However, other means may be used to remove the stent.

Although placement is described above with the retention members taking on a particular shape, in vivo, for example, upon removal of a guide wire or delivery device, or upon emergence from a channel (e.g., due to elastic rebound of the material), the shape may also be attained by application of an external stimulus such as heat or light (e.g., where a shape memory material such as a heat or light activated shape memory polymer is employed). The heat or light may be applied prior to or after the desired length of the medical device is adjusted.

Additional or alternative materials, coatings, fillers, agents, retention structures and like suitable for the devices of the present disclosure are known in the art and may be applied hereto, including as described in U.S. Pat. Nos. 8,728,169; 8,597,367; 7,951,206; and 5,681,274, assigned to Boston Scientific Corporation, the entire disclosures of which are incorporated herein by reference.

Devices according to the embodiments described, and in accordance with other embodiments of the present disclosure, alone or in a system or kit or as part of a method or procedure, including with other accessories, may be used in cavities, lumens, tracts, vessels and organs of the body, aside from stenting the ureter, such as procedures to drain, access or otherwise treat or diagnose conditions in the peritoneal, abdominal, bronchial or thoracic cavities, vascular vessels, gastrointestinal or urinary tract, uterus, bladder, lung and liver organs, etc.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. A ureteral stent comprising:
an elongated flexible tubular member having a lumen extending along a length thereof, the tubular member defining a bladder retention member at a first end thereof and a renal retention member at a second end thereof and an intermediate portion therebetween;
wherein the bladder retention member comprises:
multiple turns within a plane in which the intermediate portion lies; and
a plurality of portions configured, shaped, and structured to facilitate segmenting of the bladder retention member in vivo; and
wherein:

the bladder retention member includes radiopaque markings which are identifiable in vivo and positioned to identify the plurality of portions of the bladder retention member in vivo; and each of the plurality of portions of the bladder retention member is positioned at a respective one of the radiopaque markings along the bladder retention member which is identifiable in vivo, the bladder retention member portions and radiopaque markings together structured and configured and positioned to facilitate incremental segmenting of the bladder retention member in vivo to adjust a length of the bladder retention member in vivo in segments corresponding to the incremental portions identified by the radiopaque markings.

2. The ureteral stent of claim 1, wherein the bladder retention member is configured to return to a coiled configuration after being straightened for cutting along one of the plurality of portions.

3. The medical device of claim 2, wherein the bladder retention member comprises shape memory material returning the bladder retention member to a multi-turn coil upon removal of a straightening force therefrom.

4. The ureteral stent of claim 1, wherein the bladder retention member comprises graduated markings along the length thereof identifying the plurality of portions.

5. The medical device of claim 1, wherein the plurality of portions are structured to facilitate segmenting of the bladder retention member in vivo by including one or more of a reduced diameter of the bladder retention member, perforations of the bladder retention member, or scoring of the bladder retention member.

6. The medical device of claim 1, wherein each of the multiple turns of the bladder retention member is wound about a common turn axis that is transverse to the longitudinal axis of the intermediate portion.

7. The medical device of claim 1, wherein the renal retention member is wound in a pigtail configuration.

8. A system for facilitating drainage from the kidney to the bladder, the system comprising:
   a ureteral stent comprising an elongated flexible tubular member having a lumen extending along a length thereof, the tubular member defining a bladder retention member at a first end thereof and a renal retention member at a second end thereof and an intermediate portion therebetween;
   a delivery device configured to deliver the bladder retention member in a patient's bladder, the intermediate portion in the patient's ureter, and the renal retention member in the patient's kidney; and
   a segmenting member configured for delivery into the patient's bladder to segment the bladder retention member along one of a plurality of portions configured, shaped, and structured to facilitate segmenting of the bladder retention member in vivo;
wherein:
   the bladder retention member comprises multiple turns within a plane in which the intermediate portion lies, and a plurality of portions configured, shaped, and structured to facilitate segmenting of the bladder retention member in vivo;
   the bladder retention member includes radiopaque markings which are identifiable in vivo and positioned to identify the plurality of portions of the bladder retention member in vivo; and
   each of the plurality of portions of the bladder retention member is positioned at a respective one of the radiopaque markings along the bladder retention member which is identifiable in vivo, the bladder retention member portions and radiopaque markings together structured and configured and positioned to facilitate incremental segmenting of the bladder retention member in vivo to adjust a length of the bladder retention member in vivo in segments corresponding to the incremental portions identified by the radiopaque markings.

9. The system of claim 8, wherein the plurality of portions include one or more of a reduced diameter of the bladder detention member, perforations of the bladder retention member, or scoring of the bladder retention member.

10. The system of claim 8, wherein the delivery device straightens the ureteral stent for cutting in vivo.

11. The system of claim 10, wherein the delivery device is a guidewire.

12. The system of claim 8, further comprising a guidewire extending through the ureteral stent to facilitate delivery of the ureteral stent.

13. The system of claim 12, wherein the guidewire straightens the ureteral stent for cutting in vivo.

14. The system of claim 8, wherein the delivery device comprises an inner elongate delivery member, the ureteral stent slidably disposed coaxially about an exterior surface of the inner elongate delivery member for placement of the ureteral stent in a ureter.

15. The system of claim 14, further comprising an outer elongate pusher member slidably disposed coaxially about the inner elongate delivery member proximal to the ureteral stent, the pusher configured to abut the proximal end of the ureteral stent and push it distally along the inner member during placement.

* * * * *